United States Patent
Hepworth et al.

(10) Patent No.: US 10,246,522 B2
(45) Date of Patent: *Apr. 2, 2019

(54) CELLULOSE PARTICULATE MATERIAL

(71) Applicant: CELLUCOMP LIMITED, Burntisland (GB)

(72) Inventors: David Hepworth, Burntisland (GB); Eric Whale, Burntisland (GB)

(73) Assignee: CELLUCOMP LIMITED, Burntisland (GB)

( * ) Notice: Subject to any disclaimer, the term of this patent is extended or adjusted under 35 U.S.C. 154(b) by 613 days.

This patent is subject to a terminal disclaimer.

(21) Appl. No.: 14/778,368

(22) PCT Filed: Mar. 18, 2014

(86) PCT No.: PCT/GB2014/050859
§ 371 (c)(1),
(2) Date: Sep. 18, 2015

(87) PCT Pub. No.: WO2014/147393
PCT Pub. Date: Sep. 25, 2014

(65) Prior Publication Data
US 2016/0168274 A1    Jun. 16, 2016

(30) Foreign Application Priority Data
Mar. 18, 2013  (GB) .................... 1304939.0

(51) Int. Cl.
*C08B 15/00*    (2006.01)
*C08H 8/00*    (2010.01)
(Continued)

(52) U.S. Cl.
CPC ............ *C08B 15/00* (2013.01); *A23L 29/262* (2016.08); *A23L 33/24* (2016.08); *A61K 8/0241* (2013.01);
(Continued)

(58) Field of Classification Search
None
See application file for complete search history.

(56) References Cited

U.S. PATENT DOCUMENTS

| 2,368,527 A | 1/1945 | Edelstein |
| 4,806,475 A | 2/1989 | Gould |

(Continued)

FOREIGN PATENT DOCUMENTS

| DE | 10151952 A1 | 4/2003 |
| EP | 0402280 A1 | 12/1990 |

(Continued)

OTHER PUBLICATIONS

Caenn et al. "Drilling Fluids: State of the Art," *Journal of Petroleum Science and Engineering*, 1996, 14:221-230.
(Continued)

*Primary Examiner* — Melvin C. Mayes
*Assistant Examiner* — Stefanie J Cohen
(74) *Attorney, Agent, or Firm* — Pepper Hamilton LLP

(57) ABSTRACT

The invention relates to plant-derived cellulose-containing particles useful as strengthening agents in water based systems and to a process for preparing cellulose-containing particles from plant material, which process involves treating said plant material with a peroxide reagent. The process can be controlled to produce cellulose-containing particle having a viscosity up to about 2500 cps.

19 Claims, 1 Drawing Sheet

(51) Int. Cl.

| | | |
|---|---|---|
| C08L 1/02 | (2006.01) | |
| C08L 97/02 | (2006.01) | |
| C04B 24/38 | (2006.01) | |
| C04B 28/02 | (2006.01) | |
| C04B 18/24 | (2006.01) | |
| C09D 5/02 | (2006.01) | |
| C09D 101/02 | (2006.01) | |
| C09D 197/02 | (2006.01) | |
| D21H 17/02 | (2006.01) | |
| D21H 17/24 | (2006.01) | |
| D21H 17/25 | (2006.01) | |
| D21H 21/14 | (2006.01) | |
| A61K 8/73 | (2006.01) | |
| A61Q 19/00 | (2006.01) | |
| A61K 8/97 | (2017.01) | |
| A61K 8/02 | (2006.01) | |
| A23L 29/262 | (2016.01) | |
| A23L 33/24 | (2016.01) | |
| C09D 7/43 | (2018.01) | |

(52) U.S. Cl.
CPC .............. *A61K 8/731* (2013.01); *A61K 8/97* (2013.01); *A61Q 19/00* (2013.01); *C04B 18/248* (2013.01); *C04B 24/383* (2013.01); *C04B 28/02* (2013.01); *C08H 8/00* (2013.01); *C08L 1/02* (2013.01); *C08L 97/02* (2013.01); *C09D 5/024* (2013.01); *C09D 7/43* (2018.01); *C09D 101/02* (2013.01); *C09D 197/02* (2013.01); *D21H 17/02* (2013.01); *D21H 17/24* (2013.01); *D21H 17/25* (2013.01); *D21H 21/14* (2013.01); *A23V 2002/00* (2013.01); *A61K 2800/10* (2013.01); *A61K 2800/412* (2013.01); *C08L 2205/18* (2013.01); *Y02W 30/97* (2015.05)

(56) References Cited

U.S. PATENT DOCUMENTS

| | | | |
|---|---|---|---|
| 6,348,436 | B1 | 2/2002 | Langlois et al. |
| 7,815,841 | B2 * | 10/2010 | Merkley ................. C04B 18/24 106/731 |
| 2002/0198293 | A1 * | 12/2002 | Craun ...................... C08L 1/02 524/47 |
| 2003/0186036 | A1 | 10/2003 | Goodell et al. |
| 2006/0124124 | A1 | 6/2006 | Soni et al. |
| 2006/0289132 | A1 | 12/2006 | Heijnesson-Hulten |
| 2008/0193590 | A1 * | 8/2008 | Lundberg ............... A21D 2/188 426/2 |
| 2009/0269376 | A1 * | 10/2009 | Lundberg ............... A61K 8/731 424/401 |
| 2013/0066291 | A1 | 3/2013 | Tan et al. |
| 2016/0168273 | A1 | 6/2016 | Hepworth et al. |

FOREIGN PATENT DOCUMENTS

| | | | |
|---|---|---|---|
| EP | 0722010 | A1 | 7/1996 |
| FR | 2838531 | A1 | 5/2010 |
| GB | 577562 | A | 5/1946 |
| WO | WO 96/024720 | A1 | 8/1996 |
| WO | WO 2003/000071 | A1 | 1/2003 |
| WO | WO 2005/092815 | A1 | 10/2005 |
| WO | WO 2007/001229 | A1 | 1/2007 |

OTHER PUBLICATIONS

Dolz et al. "Flow and Thixotrophy of Non-Contaminating Oil Drilling Fluids Formulated with Bentonite and Sodium Carboxymethyl Cellulose," *Journal of Petroleum Science and Engineering*, 2007, 57:294-302.

International Search Report and Written Opinion dated May 30, 2014 for PCT/GB2014/050858.

International Search Report and Written Opinion dated May 30, 2014 for PCT/GB2014/050859.

Seres et al. "Application of Decolorization on Sugar Beet Pulp in Bread Production," *Eur. Food Res. Technol.*, 2005, 221(1-2):54-60.

UK Search Report dated Jan. 9, 2014 for GB 1304939.0.

\* cited by examiner

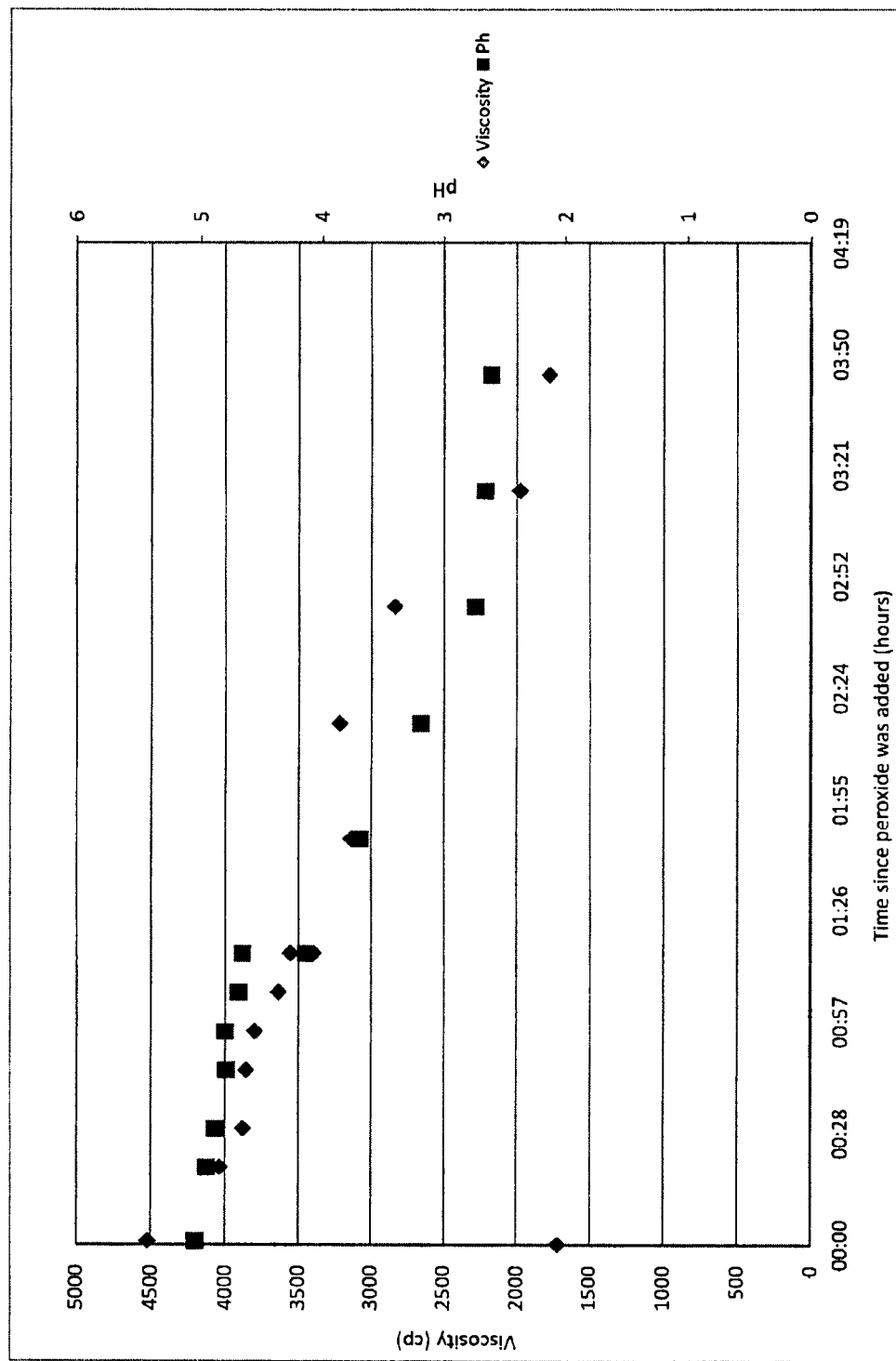

CELLULOSE PARTICULATE MATERIAL

CLAIM OF PRIORITY

This application is a U.S. national stage filing under 35 U.S.C. § 371 of International Application No. PCT/GB2014/050859 filed on Mar. 18, 2014 entitled "CELLULOSE PARTICULATE MATERIAL," which claims priority from Great Britain Patent Application Number 1304939.0 filed on Mar. 18, 2013, both of which are incorporated herein by reference in their entirety.

FIELD OF THE INVENTION

The present invention relates to a process for preparing cellulose-containing particles from plant material using a peroxide reagent, the particles, and compositions comprising the particles. The process can be controlled to provide cellulose-containing particles having a viscosity in water falling within a wide range. The cellulose-containing particles can be useful as rheology modifiers and strengthening agents in water-based systems such as paints.

BACKGROUND TO THE INVENTION

Cellulose forms the basic structural component of plant cell walls where it exists in the form of cellulose fibres. The use of cellulose extracted from plant material attracts interest because, generally, the cellulose has good strength, stiffness, biodegradability and renewability properties. It is known to reinforce materials such as plastics materials and epoxy resins, with coarse plant fibres from hemp and flax, for example. It is known to use chemically modified cellulose, such as hydroxyethyl cellulose, to increase the viscosity of an aqueous medium such as an emulsion.

However, the production of such chemically modified cellulose is energy intensive, involving a number of treatment steps. Cellulose fibres can be broken down to the substructures of microfibrils and nanofibrils. More recently, the use of these highly purified cellulose substructures as additives for modifying the physical properties of a material has attracted interest. In particular, it is known that some microfibrilar and nanofibrilar cellulose compositions can have a high viscosity in water. Such high viscosity compositions could be useful as viscosity modifiers.

The processing of untreated plant material to obtain microfibrillar and nanofibrillar cellulose compositions is also energy intensive and involves a number of stages including various chemical treatments and homogenisation through, for example, shear mixing or high pressure release or through grinding, filtration and pressing. Generally, the larger the number of process stages required, the more energy is required to produce the end product. There is a need for alternative and/or improved viscosity modifiers. There is a need to provide an alternative cellulose-containing material that can be produced from plants and that can be used as a viscosity modifier. There is a need to provide a simpler, less energy-intensive process of producing high viscosity cellulose-containing material from plants. Also, some of the commonly used chemical treatment steps, such as acid or alkali hydrolysis of plant material, can take a long time. There is a need to provide a more efficient process for extracting a useful cellulose-containing material from plants. More particularly, there is a need to provide a more efficient process of producing a high viscosity cellulose-containing material from plants.

Most known processes of producing cellulose-containing compositions from plants produce a composition having a particular characteristic viscosity or a narrow range of viscosities as measured at a particular concentration in water. Thus, in order to produce a wide range of different viscosity grades of cellulose-containing material, the manufacturer has to change between different reaction systems. This may involve the cleaning of a reactor in order to change reaction systems and product. This has wastage implications, both in terms of downtime and loss of reagents. It would be advantageous to have one reaction system for the breakdown of plant material that could be easily controlled to produce cellulose-containing material having a predetermined viscosity chosen from a wide range of possible viscosities.

Further, it is desirable that the wide range of viscosities are a wide range of viscosities that can be achieved by the material at low concentrations in water, such as 1 wt % or less (unless specified otherwise, all references to weight (wt) herein are references to dry weight). This is not easily achieved as the chemical/biological breakdown of plant material involves complex mechanisms which are not fully understood. It is also desirable to provide a process for preparing cellulose-containing material which process is capable of providing and can be controlled to provide cellulose-containing compositions of different viscosities, i.e. can be controlled to provide both cellulose-containing compositions having a relatively high viscosity at low concentrations in water and cellulose compositions having a relatively low viscosity at low concentrations in water.

For many of the end uses of cellulose-containing material processed from plants, it is necessary to decolourise the material to some extent. Decolourising cellulose-containing material produced from plants often involves additional chemical/biological treatments which increase the overall processing time and may reduce yields. It is therefore desirable to provide an improved and efficient process for preparing such processed plant material which process involves decolourising the material. It is also desirable to provide a process for preparing cellulose-containing material which process involves decolourising the material and which process can be controlled to provide cellulose-containing compositions of different viscosities. There is also a need for a process for preparing high viscosity cellulose-containing material from plants which process also involves decolourising the material.

The present invention seeks to provide a new method of producing cellulose-containing material from plant matter which alleviates one or more of the above problems. Further the invention seeks to provide new compositions comprising cellulose and uses for same.

SUMMARY OF THE INVENTION

The present invention relates to a plant-derived cellulose-containing particulate material. The cellulose-containing particles comprise plant cell wall material and are useful as rheology modifiers in water-based systems.

According to a first aspect of the invention there is provided a plant-derived cellulose particulate material comprising less than 30 wt % extractable glucose; extractable xylose in an amount of at least 3% of the amount of extractable xylose in the starting plant material, and a cellulose content of less than 60% by dry weight.

According to a second aspect of the invention there is provided a process for preparing cellulose-containing particulate material which has a viscosity at a concentration of 1 dry wt % in water of less than 2500 cps, the process comprising the steps of:
(i) contacting herbaceous plant material with a peroxide reagent and water;
(ii) heating the mixture from (i) to a temperature of from 30 to 110° C. and maintaining said mixture at a temperature of from 30 to 110° C. until the pH of the mixture has dropped by at least about 2 pH units; and
(iii) isolating the cellulose-containing particles.

Advantageously, in the second aspect of the invention, the use of a peroxide reagent to treat plant material has been found to be extremely effective in producing the cellulose-containing particles of the first aspect and, in particular, low to medium viscosity cellulose-containing particles. The process of the invention employs the use of only one chemical reagent to break down the vegetable material, the peroxide reagent, and thus is a relatively simple, efficient process. Further, the process of the invention can be controlled relatively easily to produce cellulose-containing particles having a relatively low viscosity in water. In particular, the viscosity of the cellulose-containing particles can be controlled by monitoring the pH of the reaction mixture of step (ii). Also the process of the invention can be controlled to provide decolourised cellulose-containing particles without having to use any additional chemical/biological reagents.

A third aspect of the invention relates to the cellulose-containing particles obtainable by the process of the invention.

In the process of the invention the plant material is broken down to particles comprising plant cell wall material. These particles comprise plant cell wall material, retain some of the character of the plant cell walls and, importantly, have the ability to swell with water. The particles have good water-holding capabilities and this property contributes to their usefulness as viscosity modifiers in water-based systems including: coatings, such as epoxy resin-based paints; polyurethane-based paints; acrylic resin-based paints; home and personal care products such as shampoos or face creams; and concrete. They have also been found to have good shear-thinning properties and good mechanical properties, such as strength, and can beneficially reduce the porosity of paper compositions.

Further aspects of the invention relate to the use of the cellulose-containing particles, and compositions comprising the cellulose-containing particles. These are environmentally-friendly formulations.

BRIEF DESCRIPTION OF THE FIGURES

FIG. 1 is a graph of pH and viscosity versus time for the process of the invention described in Example 1.

DETAILED DESCRIPTION OF THE INVENTION

Unless otherwise stated, references herein to cellulose-containing particles and cellulose particulate material should be interpreted as any cellulose containing material resulting from the processes described herein. Such references should not be interpreted as excluding any other materials, rather that the particles contain or comprise cellulose.

Unless otherwise stated, references herein to extractable content of a monosaccharide other than glucose refer to the amount of the stated monosaccharide which can be extracted through hydrolysis of an alcohol insoluble fraction of cellulose-containing particles or cellulose particulate material when contacted with 2M trifluoroacetic acid for 4 hours at at least 100° C.

Unless otherwise stated, references herein to extractable content of glucose refer to the amount of glucose which can be extracted through hydrolysis of an alcohol insoluble fraction of cellulose-containing particles or cellulose particulate material when contacted with 72% (w/v) sulphuric acid for 4 hours at 120° C.

Unless otherwise stated, wt % values refer to the extractable amount of the specified compound isolated from a known dry mass of the particulate material following acid hydrolysis.

Unless otherwise stated, absolute % values refer to the extractable amount of the specified compound isolated from the particulate material following acid hydrolysis as a percentage of the extractable amount of the specified compound isolated from the starting plant material following acid hydrolysis.

Unless otherwise stated, references herein to the starting plant material are to the herbaceous plant material used in the process of the present invention. References to the starting plant material are also to plant material which has been homogenized to a pulp but before any chemical treatment.

Unless otherwise stated, references herein to the "peroxide process" are to the treatment of the plant material with a peroxide reagent with the application of heat. Unless otherwise stated, references herein to the "peroxide plus oxidant/bleach process" or the "full process" are to the treatment of the plant material with a peroxide reagent followed by treatment with an oxidant/bleach.

Unless otherwise stated, references herein to the viscosity of the cellulose-containing particles is the viscosity the particles at a concentration of 1% dry weight in water as measured at 20° C. using a Brookfield viscometer with RV spindles rotated at 10 rpm.

Unless otherwise stated, references herein to "high viscosity" cellulose-containing particles are to those particles having a viscosity of greater than about 2500 cps when measured according the method described above.

Unless otherwise stated, references herein to "low viscosity" cellulose-containing particles are to those particles having a viscosity of less than about 2000 cps, for example less than about 1000 cps, when measured according the method described above.

Unless otherwise stated, the term "about" is used to provide flexibility to a numerical range endpoint by providing that a given value may be a little above or a little below the endpoint to allow for variation in test methods or apparatus. The degree of flexibility of this term can be dictated by the particular variable and would be within the knowledge of those skilled in the art to determine based on experience and the associated description herein.

Cellulose-Containing Particles

The first aspect of the present invention provides a plant-derived cellulose particulate material comprising less than 30 wt % extractable glucose; and extractable xylose in an amount of at least 3% of the amount of extractable xylose in the starting plant material.

In the process of the invention, the plant material is broken down to cellulose-containing particles comprising plant cell wall material. Plant cell wall material comprises cellulose, hemicelluloses (such as xyloglucans, xylans, mannans and glucomannans), pectins, and proteins such as glycoproteins. The particles can include plant cells, plant cell walls and loose associations of plant cell wall polymeric components, which can be, for example, pieces of a gel formed from cellulose, hemicellulose, pectin and protein. It is believed that, in the process of the invention, plant cell wall breakdown occurs through partial degradation of pectins and hemicelluloses and subsequent extraction of pectinic and hemicellulosic monosaccharides. However, it is believed that the process of the present invention does not degrade the cellulosic material such that some of the cell wall character/structure is retained. It is also believed that the peroxide reagent cleaves covalent bonds within the cell wall polysaccharide structure, loosening up the cell wall structure, with a result that the cellulose-containing particles of the invention are capable of swelling with water. This ability to swell with water contributes to the advantageous rheology-modifying properties that the particles of the present invention exhibit.

The cellulose-containing particles are insoluble in water. By insoluble in water is meant that, at a concentration of 1 wt % (solids) or less in water, the cellulose-containing particles are discrete particles. A discrete particle is one that can be observed as such using light microscopy at 100× magnification. The cellulose-containing particles preferably have a mean major dimension of from 1 to 250 µm. The particles can have a mean major dimension which is greater than 10 µm and up to 200 µm. Preferably they have a mean major dimension of from 10 to 70 µm or from 30 to 70 µm. The mean major dimension can be measured by light microscopy. The particles are stained by adding a few drops of methylene blue to a dilute suspension of fully hydrated particles on a slide. The particles are viewed at 100× magnification, using a Dyno-eye camera (USB) on the eye piece of the microscope with Dynocapture 2.0 software on a computer connected to the camera. The largest particle dimension is measured using image analysis.

Preferably the cellulose-containing particles contain less than 5 wt %, preferably less than 3 wt %, of microfibrillar material as measured by the amount of material that passes through a 10 µm filter after repeated washing following by drying of the washings at 150° C.

The cellulose-containing particles preferably comprise cellulose in an amount of less than 60 wt %, preferably up to 59 wt %, more preferably up to 55 wt %. Preferably the cellulose-containing particles contain cellulose in an amount of at least 40 wt % or 45 wt %. In one embodiment, the cellulose-containing particles comprise cellulose in an amount of 50 to less than 60 wt % or in an amount of less 53 to 58 wt %.

In one embodiment, the cellulose-containing particles comprise cellulose in an amount less than about 60 wt %, for example less than about 59 wt %, less than about 58 wt %, less than about 55 wt %, less than about 53 wt %, less than about 50 wt %, less than about 45 wt %, less than about 40 wt %.

In one embodiment, the cellulose-containing particles comprise cellulose in an amount greater than about 40 wt %, for example greater than about 45 wt %, greater than about 50 wt %, greater than about 53 wt %, greater than about 55 wt %, greater than about 58 wt %, greater than about 59 wt %, for example up to about 60 wt %.

Preferably the cellulose-containing particles contain polysaccharides other than cellulose in an amount of from 4 to 6 wt %.

Preferably the cellulose-containing particles contain hemicellulose in an amount of less than 2 wt % and the pectin in amount of less than 10 wt %. The cellulose content and the content of the other polysaccharides may be measured using the following standard method: a sample of the material is converted into alcohol-insoluble residues and a portion of this is then subjected to acid hydrolysis using 2M trifluoroacetic acid for 1 hour at 120° C. This produces a hydrolysate and a non-hydrolysable cellulosic/polysaccharide residue. The hydrolysate is dried and re-suspended in distilled water. This solution is then analysed for monosaccharide content using HPLC.

The cellulose particulate material contains extractable xylose in an amount of at least 3 wt %, for example at least 5% of the amount of extractable xylose in the starting plant material. Alternatively, the cellulose particulate material contains at least 10% of the amount of extractable xylose in the starting plant material, for example at least 20%, at least 30%, at least 40% extractable xylose of the amount of extractable xylose in the starting plant material.

Alternatively, the cellulose particulate material contains at least 3 wt %, for example at least 5% extractable xylose relative to the amount of extractable xylose in the starting plant material. Alternatively, the cellulose particulate material contains at least 10% extractable xylose relative to the amount of extractable xylose in the starting plant material, for example at least 20%, at least 30%, at least 40% extractable xylose relative to the amount of extractable xylose in the starting plant material.

Alternatively, the cellulose particulate material contains extractable xylose in an amount of at least 4% of the amount of extractable xylose in the starting plant material. Alternatively, the cellulose particulate material contains at least 5% of the amount of extractable xylose in the starting plant material, for example at least 6%, at least 7%, at least 8%, at least 9% extractable xylose of the amount of extractable xylose in the starting plant material.

Alternatively, the cellulose particulate material contains extractable xylose in an amount of less than 10% of the amount of extractable xylose in the starting plant material. Alternatively, the cellulose particulate material contains less than 9% of the amount of extractable xylose in the starting plant material, for example less than 8%, less than 7%, less than 6%, less than 5%, less than 4% extractable xylose of the amount of extractable xylose in the starting plant material.

Alternatively, the cellulose particulate material contains less than 70% extractable xylose relative to the amount of extractable xylose in the starting plant material.

Alternatively, the cellulose particulate material contains less than 60% extractable xylose relative to the amount of extractable xylose in the starting plant material, for example less than 55% extractable xylose relative to the amount of extractable xylose in the starting plant material.

In an alternative embodiment, the cellulose particulate material is derived from sugar beet and contains at least about 0.5 wt %, for example at least about 1 wt %, at least about 1.5 wt %, for example at least about 1.6 wt %, at least about 1.7 wt %, at least about 1.8 wt % at least about 1.9 wt %, for example about 2 wt % extractable xylose.

In an alternative embodiment, the cellulose particulate material is derived from sugar beet and contains at least about 0.5 wt %, for example at least about 1 wt %, at least about 1.5 wt %, for example at least about 1.6 wt %, at least about 1.7 wt %, at least about 1.8 wt % at least about 1.9 wt %, for example about 2 wt % extractable xylose when the amount of extractable xylose in the starting sugar beet plant material is about 20 wt %.

In an alternative embodiment, the cellulose particulate material is derived from carrot and contains at least about 0.8 wt %, for example at least about 0.9 wt %, for example about 1.0 wt % extractable xylose when the amount of extractable xylose in the starting carrot plant material is about 2.0 wt %.

The cellulose particulate material contains less than 30 wt % extractable glucose. Alternatively, the cellulose particulate material contains less than 25 wt % extractable glucose, for example less than 20 wt %, less than 19 wt %, less than 18 wt %, less than 17 wt %, less than 16 wt %, less than 15 wt % extractable glucose.

In an alternative embodiment, the cellulose particulate material is derived from sugar beet and contains less than about 25 wt %, for example less than about 20 wt %, less than about 15 wt %, for example about 13 wt % extractable glucose when the amount of extractable glucose in the starting sugar beet plant material is about 7 wt %.

In an alternative embodiment, the cellulose particulate material is derived from carrot and contains less than about 25 wt %, for example less than about 20 wt %, for example about 19 wt % extractable glucose when the amount of extractable glucose in the starting carrot plant material is about 11 wt %.

In one embodiment, the cellulose particulate material contains less than about 1 wt %, for example less than about 0.5 wt %, for example less than about 0.2 wt %, for example substantially no mannose. In one embodiment, the cellulose particulate material contains less than about 1 wt %, for example less than about 0.5 wt %, for example less than about 0.2 wt %, for example substantially no rhamnose.

In one embodiment, the cellulose particulate material may comprise one or more polysaccharides from homogalacturonan, (1-4)-β-D-galactan, xyloglucan, (1-4)-β-D-xylan and (1-4)-β-D-arabinoxylan. In one embodiment, the cellulose particulate material may comprise fully methylesterified homogalacturonan, partially methylesterified homogalacturonan or fully de-esterified homogalacturonan. In one embodiment the cellulose particulate material may comprise one or more glycoproteins. For example, in one embodiment the cellulose particulate material may comprise extensin. Determination of the presence of such components can be readily carried out using the CoMPP glycoarray method as described in Møller I, Marcus S E, Haeger A, Verhertbruggen Y, Verhoef R, Schols H, Ulvskov P, Mikkelsen J D, Knox J P, Willats W. (2007) High-throughput screening of monoclonal antibodies against plant cell wall glycans by hierarchical clustering of their carbohydrate microarray binding profiles. Glycoconj J. 25(1): 37-48.

The cellulose-containing particles preferably comprise a non-saccharide (i.e. non-carbohydrate) component which is present in an amount of 20 to 50, preferably 35 to 48 wt %. This component may comprise proteins, e.g. glycoproteins.

The cellulose-containing particles can be hydrated and preferably have water-holding capacities of 90 to 99.5 wt % water. The water-holding capacity is measured by dispersing the particles in water, letting them fully hydrate, then filtering them out using a 10 μm filter paper, with no pressure applied during filtering. The material collected in the filter once the liquid has ceased to drain out is weighed, then dried using a moisture analyser set to 150° C., and then reweighed to determine the amount of water present.

The cellulose-containing particles may have a viscosity of up to 2500 cps, for example up to 1000 cps and preferably have a viscosity of at least 10 or at least 100 cps. In this embodiment, the particles can have a water-holding capacity in the range of 93 to 96 wt % water. Preferably, they have a mean major dimension of from 10 to 70 μm or to 100 μm and comprise cellulose in an amount of 45 or 50 to less than 60 wt %. These low viscosity cellulose-containing particles are useful as viscosity improvers for water-based systems where a relatively large amount can be added to achieve a required viscosity whilst adding mechanical strength to the substantially dried and/or cured composite material resulting from the water-based system. In other words, these particles can act as a strengthening agent for a water-based system without having too strong an effect on the viscosity of the system. In addition, these particles can provide anticracking properties during the drying and curing of the paint. For example, a 3% loading by dry weight in an acrylic paint can enable a coalescent content of the paint to be reduced without causing the paint to crack during drying. This is advantageous because the coalescent is a solvent and reducing its content will improve the paint's environmental credentials. A 3% loading by dry weight in an acrylic paint also increased the scrub resistance of an acrylic paint. The low viscosity particles are also shear thinning, but start from a lower viscosity at low shear than the high viscosity material.

The cellulose-containing particles can have a viscosity of up to 7500 or 8000 cps. They may be high viscosity particles and have a viscosity of from 2500, or 3000 to 7000 cps or they may be low viscosity particles and have a viscosity of from 10 to 1000 cps.

The particles may have a viscosity of greater than about 2500 cps, for example at least about 3000 cps, for example at least about 3200 cps, at least about 3500 cps, at least about 4000 cps, at least about 5000 cps, at least about 5500 cps, at least about 6000 cps, at least about 7000 cps, at least about 7500 cps, for example up to 8000 cps.

The particles may have a viscosity of less than about 8000 cps, for example less than about 7500 cps, less than about 7000 cps, less than about 6000 cps, less than about 5500 cps, less than about 5000 cps, less than about 4000 cps, less than about 3500 cps, less than about 3200 cps, less than about 3000 cps, for example about 2500 cps.

The particles may have a viscosity of 2500 or 3000 or 4000 cps or more, preferably the particles have a viscosity of 3500 to 5500 cps. In this embodiment, the particles can have a water-holding capacity in the range of 97 to 99.5 wt % water. Preferably, they have a mean major dimension of from 10 to 70 μm or to 100 μm and comprise cellulose in an amount of 45 or 50 to less than 60 wt %. These high viscosity cellulose-containing particles are useful as viscosity improvers for water-based systems as only a relatively small amount is required to achieve a required viscosity. In addition, the viscosity of the system is increased by a large amount at low shear rates and by a lot less at high shear rates. In other words, the cellulose-containing particles are very shear-thinning in water-based systems and are useful as rheology modifiers in such systems. This can be advantageous where, for example, anti-settlement of heavy additives such as pigments are required in a static formulation, e.g. paint in a can, but where easy flow is required at high shear rates, for example, during application of the paint to a surface by spraying or brushing.

Another advantage of the cellulose-containing particles of the invention is that in water-based formulations, the particles are quite insensitive to pH, i.e. the viscosity does not measurably change between a pH of 2 to 14, for example of 3 to 12. This is in contrast to many other viscosity-modifying products such as hydroxyethylcellulose (HEC) that are sensitive to pHs in this range.

Process for Preparing Cellulose-Containing Particulate Material

Step (i)

Step (i) of the process of the invention comprises contacting herbaceous plant material with a peroxide reagent and water to provide a mixture of plant material, peroxide reagent and water.

Plant Material

The plant material used in the present invention is herbaceous plant material. "Herbaceous" is a well-defined botanical term that refers to annual, bi-annual or perennial vascular plants. These are further characterized by their aerial stems dying after each growth season. Regrowth in subsequent seasons for bi-annual and perennial species takes place from subterraneous organs, for example stem or root storage organs, tubers. This is in contrast to woody species whose stems resume growth each season and thus form growth rings. The particular property of herbaceous plants of relevance to the present invention is the abundance of primary walls in their tissues. These are in particular found in parenchymal tissues. The skilled person will be aware that no organ from a herbaceous vascular plant is made up entirely of parenchyma or entirely of primary walls, as vascular elements with their secondary walls are invariably also a component of all but the simplest organs. However, it will also be appreciated that plant material made up of polysaccharide rich primary cell walls also occurs in two groups of plants that are not vascular plants: the mosses and the charophycean green algae. "Herbaceous" shall, for the purposes of this invention, also comprise biomass from these groups of plants. The plant material used in the process of the invention therefore includes vegetables, for example root vegetables, and fruit. Examples of root vegetables include carrot, sugar beet (also herein referred to as beet) or turnip, parsnip and swede. Examples of fruit include apples, pears and grapes. The plant material may be from a potato. The plant material can be derived from one type of vegetable, for example, substantially all of the plant material can comprise material from one specific root vegetable, for example, one of carrot, sugar beet, turnip, parsnip and swede. By substantially all is meant that at least 90% by dry weight of the vegetable material. As referred to herein, all weights are dry weight unless otherwise specified. Similarly, substantially all of the plant material can comprise material form one specific fruit, for example, one of apples, pears or grapes. The plant material can be derived from a mixture of type of vegetables and fruit, for example, more than one of carrot, beet or turnip, parsnip, swede, apples, pears, and grapes. Preferably the plant material comprises one of or a mixture of sugar beet and carrot. In one embodiment, the plant material used in the process of the invention is not wood. Preferably, where the fruit or vegetable has a skin that forms greater than 3% of the weight of the fruit or vegetable, the fruit or vegetable has had the skin removed, for example, by peeling.

Preferably the plant material has a parenchymal cell content of higher than 30% by volume, more preferably higher than 35% by volume or higher than 50% by volume and most preferably higher than 70% based on the total volume of the plant material. Parenchymal cell content is determined by image analysis, i.e. cutting a section of the plant, viewing the section in a microscope and measuring the areas of parenchymal tissue. Ideally sections are taken through different parts of the plant or plant organ and these areas can then be converted into a prediction of tissue volumes. Preferably the plant material contains less than 20 wt % lignin, more preferably it contains from 1 to 10 wt % lignin, most preferably it contains from 1 to 5 wt % lignin. Lignin content can be measured by a standard method such as the Klason method. This method uses strong acid treatment to breakdown and dissolve all the plant materials except the lignin. The lignin is defined as the weight of material that cannot be broken down by 72% sulphuric acid.

In one embodiment, the herbaceous plant material comprises less than about 30 wt % lignocellulose. In one embodiment, the herbaceous plant material comprises less than about 20 wt % lignocellulose. In one embodiment, the herbaceous plant material comprises less than about 15 wt % lignocellulose. In one embodiment, the herbaceous plant material comprises less than about 10 wt % lignocellulose, for example less than about 9 wt % lignocellulose, less than about 8 wt % lignocellulose, less than about 7 wt % lignocellulose, less than about 6 wt % lignocelluloses, less than about 5 wt % lignocellulose, less than about 4 wt % lignocellulose, less than about 3 wt % lignocellulose, less than about 2 wt % lignocellulose, less than about 1 wt % lignocellulose. In one embodiment, the herbaceous plant material comprises substantially no lignocellulose.

In one embodiment of the present invention the herbaceous starting material is a seed plant, i.e. belonging to Magnoliaphyta. In a further embodiment the plant is a monocotyledon, more specifically a member of Poales, typically a cereal. The plant material may be a waste product or side-stream from agricultural production. In yet another preferred embodiment the herbaceous plant is a member of eucotyledones, more specifically a crop plant, or a waste product or side-stream from agricultural production. Pulps remaining after production of sugar beet or potato starch are attractive agricultural side streams useful for the present invention. Root crops are in general relevant raw materials. A non-exhaustive list comprises carrot, swede, turnips, parsnips and radish. Pomace from fruit preserve, jam, juice production is another valuable waste product from which cellulose may be recovered by the methods disclosed in the present invention.

The plant material may be raw plant material or raw plant material that has been heat treated and/or mechanically treated, it is preferably washed but is, preferably, otherwise essentially untreated. Preferably, it will not have been treated by any chemical reagents which could act to break it down. Preferably, it will not have been subjected to acid or alkali hydrolysis treatment. Preferably the plant material has been mechanically treated, e.g. chopped/shredded so that it is in the form of particles having a mean major dimension of, for example, less than 10 mm, preferably less than 500 μm, more preferably less than 250 μm, most preferably less than 200 μm. The plant material can be in the form of a pulp, for example, taken from an industrial waste stream. The pulp can be prepared from raw plant matter by washing the raw plant matter, shredding or chopping it, cooking it in water at, for example, 90 to 100° C. until soft and optionally homogenising it to reduce the size of the insoluble particles contained therein. Alternatively, the pulp can be prepared from raw plant matter by washing the raw plant matter, shredding or chopping it, cooking it in water in a pressure cooker until soft and optionally homogenising it to reduce the size of the insoluble particles contained therein. It will be recognised that the cooking temperature in this embodiment can exceed 100° C.

Preferably the insoluble particles of the pulp have a mean major dimension of less than 10 mm, preferably less than 500 μm, preferably less than 250 μm, more preferably less than 200 μm. The pulp can be washed and filtered to remove soluble by-products. In one embodiment, step (i) comprises providing a mixture of plant material, peroxide reagent and water, wherein the plant material is made up of particles having a mean major dimension of less than 500 µm. Step (i) can comprise preparing pulp from raw plant material and adding peroxide reagent and water to it. In another embodiment, step (i) can comprise providing a mixture of raw plant material, peroxide reagent and water and homogenising the mixture until the plant material is made up of particles having a mean major dimension of less than 500 µm.

The speed at which the process of the invention proceeds depends, in part, upon the concentration of the reactants. Preferably, the concentration of the plant material in the mixture of step (i) is kept to a level at which the process can be readily controlled. In one embodiment the mixture of step (i) comprises plant material in a concentration of from 1 to 10 wt % based on the combined amount of water and plant material present. Preferably, this concentration is from 1 to 7 wt %, more preferably from 2 to 5 wt %.

Peroxide Reagent

The process of the invention utilises a peroxide reagent to break down the plant material and to decolourise it. Preferably the peroxide reagent is chosen from hydrogen peroxide, an organic peroxide or an inorganic peroxide. More preferably the peroxide reagent is hydrogen peroxide or an organic peroxide. Examples of suitable organic peroxides are peroxycarboxylic acids such as peracetic acid and meta-chloroperoxybenzoic acid and organic hydroperoxides such as benzylperoxide. Examples of suitable inorganic peroxides include ionic peroxide salts, e.g. peroxides of the alkali and alkaline earth metals and acid peroxides such as peroxysulfuric acid and peroxyphosphoric acid. Most preferably, the peroxide reagent is hydrogen peroxide. The peroxide reagent is preferably present in an amount of between 5 to 40 wt % based on the dry matter weight of the plant material. In one embodiment the peroxide reagent is present in an amount of between 20 to 35 wt % based on the weight of the plant material. In one embodiment the peroxide is added as 35% aqueous solution and the ratio of peroxide reagent solution to dry solids content of plant material is at least about 0.25:1 (by mass), for example at least about 0.5:1, at least about 0.6:1, at least about 0.7:1, at least about 0.8:1, at least about 0.9:1, for example about 1:1.

In the process of the present invention, it is believed that the peroxide reagent acts to loosen the natural cell wall structure by breaking certain bonds within the complex structure of the cell wall allowing it to hydrate (and swell) more with water and greatly increasing the viscosity of the plant material. This effect, the extent and speed of it, has not been observed using acid or alkali hydrolysis of vegetable material. In addition, it has been found that high viscosity cellulose-containing particles can be obtained efficiently by the process of the present invention, with the use a single chemical treatment step on the plant material. Preferably the process does not comprise any additional chemical treatments and/or any biological, e.g. enzymatic treatments.

A catalyst for catalysing the reaction of the peroxide reagent with the plant material can be added to the mixture of step (i). Examples of catalysts include manganese catalysts. Thus the mixture of step (i) can also comprise a peroxide reagent catalyst. However, in one embodiment, the process of the present invention is carried out in the absence of a catalyst.

Step (ii)

Step (ii) involves heating the mixture provided in step (i). In this step the plant material is broken down by the peroxide reagent and also decolourisation of the cellulose-containing particles can occur.

In step (ii), the mixture is heated to a temperature of from 30 to 110° C., for example 30 and 100° C., and maintained at a temperature of from 30 to 110° C., for example 30 and 100° C. for a period of time. The period of time that the mixture is maintained within this temperature range can be between 1 minute and 6 hours. In one embodiment, the mixture is maintained at a temperature of from 30 to 110° C., for example 30 to 100° C., for less than 6 hours, for example less than 5 hours, less than 4 hours, less than 3 hours, less than 2 hours, for example less than 1 hour. Alternatively, the mixture is maintained at a temperature of from 30 to 110° C., for example 30 to 100° C., for at least 1 hour, for example at least 2 hours, at least 3 hours, at least 4 hours, at least 5 hours, at least 6 hours. In one embodiment, the mixture is kept at a steady temperature within the range of 30 to 110° C., for example 30 to 100° C., for the period of time. In another embodiment, the temperature of the mixture can be varied within the range of 30 to 110° C., for example 30 to 100° C., for the period of time, i.e., increased and/or decreased during this period of time, but still remaining within the range of from 30 to 110° C., for example 30 and 100° C. The choice of temperature(s) and the period of time the mixture is kept at the temperature(s) depend on the desired viscosity of the cellulose-containing particles and, optionally, the desired degree of decolourisation. Preferably the mixture is heated to a temperature of from 70 and 100° C. and maintained at a temperature of from 70 and 100° C. for a period of time as specified above.

Viscosity

The inventors have investigated the viscosity behaviour of the cellulose-containing particles as a function of the pH of the mixture of step (ii) which is being held at a temperature of between 30 to 110° C., for example 30 and 100° C., for a period of time. We refer to FIG. 1 from which it can be seen that for the process carried out in Example 1, the pH of the reaction mixture varies with time and with the viscosity of the cellulose-containing particles. In one embodiment, the period of time the mixture is maintained at a temperature of between 30 to 110° C., for example 30 and 100° C., can be determined by monitoring the pH of the reaction liquid of the reaction mixture of step (ii). The present inventors have found that the pH of the mixture varies as the viscosity of the cellulose-containing particles varies and thus this pH measurement can provide an indicator of the viscosity of the cellulose-containing particles produced. It is believed that, advantageously, this pH-viscosity correlation is independent of the temperature that the mixture of step (ii) is heated to/kept at. Thus the correlation can be applied to reaction systems with different heating regimes. However, the pH-viscosity correlation may vary if the type of plant material changes.

Thus in a preferred embodiment of the present invention, the mixture is maintained at a temperature of between 30 to 110° C., for example 30 and 100° C., until it has a predetermined pH value in order to produce cellulose-containing particles having a desired viscosity. The pH value can be determined by a calibration run carried out under the same conditions.

Disclosed herein is a process comprising:
(i) providing a mixture of plant material, peroxide reagent and water;
(ii) heating said mixture to a temperature in the range of from 30 to 100° C. and maintaining said mixture at a temperature in the range of from 30 to 100° C. for a period of time in order to break down the plant material; and (iii) isolating a residue comprising cellulose-containing particles,
wherein said process comprises monitoring the pH of the mixture during step (ii) and terminating the maintaining of the mixture at a temperature in the range of from 30 to 100° C. when the mixture reaches a predetermined pH value.

In this embodiment said pH value can be determined from a calibration giving the viscosity in water of the cellulose-containing particles to be expected as a function of pH of the reaction mixture in step (ii). Thus one example of the process comprises performing a calibration whereby the process is carried out several times under the same conditions except that the period of time at which the mixture of step (ii) is maintained at a temperature of from 30 to 110° C., for example 30 to 100° C., is varied. Each time the reaction mixture is sampled. The pH is first measured and the sample then separated into an insoluble residue containing the cellulose-containing particles and a reaction liquid component. The viscosity in water of the cellulose-containing particles is measured and a correlation between viscosity of the cellulose-containing particles and pH of reaction mixture of step (ii) can thus be obtained.

In particular, the present inventors have found that the pH value drops as the viscosity decreases. Therefore in the process described above, the predetermined pH is Y wherein Y=X−Δ wherein X is the pH of the mixture of step (ii) at the start of the heating process and 0<Δ<4. For cellulose-containing particles with a higher viscosity, 0<Δ<2. In another embodiment, 2<Δ<4, and this gives a cellulose-containing particles with a lower viscosity. For carrot as a raw material at a 5 wt % concentration based on the water and plant material in the mixture of step (i): when 0<Δ<4, cellulose-containing particles having a viscosity in the range of 10 to 6800 cps can be obtained; when 0<Δ<1, cellulose-containing particles having a viscosity in the range of 5000 to 3200 cps can be obtained; when 1<Δ<2, cellulose-containing particles having a viscosity in the range of 3200 to less than 2500 cps can be obtained; and when 2<Δ<4, cellulose-containing particles having a viscosity in the range of 2500 to less than 100 cps can be obtained.

Thus, in one embodiment, step (ii) of the process may be maintained until the pH of the mixture has fallen by at least 2 pH units relative to the starting pH, for example the pH of the mixture has fallen by at least about 3 pH units relative to the starting pH, for example the pH of the mixture has fallen by about 4 pH units relative to the starting pH. Alternatively, step (ii) of the process may be maintained until the pH of the mixture has fallen by less than about 4 pH units relative to the starting pH, for example the pH of the mixture has fallen by less than about 3 pH units relative to the starting pH, for example the pH of the mixture has fallen by about 2 pH units relative to the starting pH.

Thus, in one embodiment, step (ii) of the process may be maintained until the pH of the mixture has fallen by less than about 2 pH unit relative to the starting pH, for example the pH of the mixture has fallen by less than about 1.9 pH units relative to the starting pH, for example the pH of the mixture has fallen by less than about 1.75 pH units relative to the starting pH, less than about 1.5 pH units, less than about 1.4 pH units, less than about 1.3 pH units, less than about 1.2 pH units, less than about 1.1 pH units, for example about 1 pH unit. Alternatively, step (ii) of the process may be maintained until the pH of the mixture has fallen by at least about 1 pH unit, for example at least about 1.1 pH units, at least about 1.2 pH units, at least about 1.4 pH units, at least about 1.5 pH units, at least about 1.75 pH units relative to the starting pH, for example the pH of the mixture has fallen by at least about 1.9 pH units relative to the starting pH, for example the pH of the mixture has fallen by about 2 pH units relative to the starting pH.

Preferably, no pH-modifying additives are added to the mixture of step (i) or step (ii) during the process. By pH-modifying is meant adjusts the pH of the mixture by a magnitude of greater than 0.5.

The present studies have involved an investigation into the viscosity behaviour of the cellulose-containing particles formed by the process of the invention as a function of the period of time the mixture of step (ii) is held at a temperature of between 30 to 110° C., for example 30 and 100° C. It has been found that the viscosity of the cellulose-containing particles does not vary linearly with time. Unless otherwise specified, as referred to herein, the viscosity of the cellulose-containing particles is the viscosity the particles at a concentration of 1% dry weight in water as measured at 20° C. using a Brookfield viscometer with RV spindles rotated at 10 rpm.

We refer to FIG. 1 from which it can be seen that for the process carried out in Example 1, the viscosity of the insoluble cellulose-containing particles formed initially increases (from ~1700 to 4500 cps) and then reduces as the reaction progresses at temperature. The higher the temperature, the more rapidly the viscosity reaches a peak value and begins to fall. Thus, it is possible, using the process of the invention, to produce cellulose-containing compositions which have very different viscosities, simply by controlling the length of time the mixture in step (ii) is held at a temperature of between 30 and 100° C.

Thus, the mixture may be maintained at a temperature of between 30 to 110° C., for example 30 and 100° C., for a predetermined period of time in order to produce particulate cellulose having a desired viscosity. The length of time can be determined by a calibration run carried out under the same conditions. The calibration may change if the concentration of the starting materials (plant material and peroxide reagent), the type of plant material or the temperature at which the reaction mixture is maintained changes.

Thus, described herein is a process which comprises:
(i) providing a mixture of plant material, peroxide reagent and water;
(ii) heating said mixture to a temperature in the range of from 30 to 100° C. and maintaining said mixture at a temperature in the range of from 30 to 100° C. a period of time in order to break down the plant material; and
(iii) isolating a residue comprising cellulose-containing particles,
wherein said period of time is chosen so as to produce cellulose-containing particles having a desired viscosity in water. In this process said period of time can be determined from a calibration which gives the viscosity in water of the cellulose-containing particles to be expected as a function of said period of time. Thus, the process may comprise performing a calibration whereby the process is carried out several times under the same conditions except that the period of time at which the mixture of step (ii) is maintained at temperature of from 30 to 100° C. is varied. Each time the reaction mixture is sampled. The sample is then separated into an insoluble residue containing the cellulose-containing particles and a reaction liquid component. The viscosity in water of the cellulose-containing particles is measured and this is correlated with said period of time.

In the process described herein higher viscosity materials are generally produced in a short reaction time, whilst lower viscosity materials are generally produced in a longer reaction time. This is a surprising finding and, as a result of this, the process to the invention can be controlled to provide cellulose-containing particles with specific viscosity properties.

Advantageously, the process described herein can produce significantly decolourised cellulose-containing particles as the peroxide reagent both breaks down the plant material and decolourises it. However, in the case of producing higher viscosity cellulose material, the reaction time can be relatively short and decolourisation may not have occurred to the maximum or the required extent. It has been found that increasing or decreasing the temperature in a series of controlled steps can help to decolourise the cellulose-containing particles while maintaining high viscosity. Thus in one embodiment, step (ii) may comprise heating the mixture to a temperature of between 90 and 100° C. and maintaining it at this temperature for some time, following by cooling the mixture to a temperature of between 75 and 85° C. and maintaining the mixture at this temperature for the rest of the period of time. Alternatively, step (ii) may comprise heating the mixture to and maintaining it at a temperature of between 75 and 85° C. for a period of time then increasing the temperature to between 90 and 100° C. and holding at this temperature for a period of time until the desired degree of decolourization has been achieved.

To achieve very high viscosity cellulose-containing particles, i.e. particles with a viscosity of 6800 cps or greater, without decolourisation of the particles, the mixture may only need to be heated to a relatively low temperature for a relatively short time. Below 30° C., it is not possible to obtain high viscosity cellulose-containing particles of the invention within a reasonable time frame, i.e. in a time frame of hours rather than days.

To achieve high viscosity cellulose-containing particles, i.e. particles with a viscosity of greater than 2500, for example 3000 cps or greater, with significant decolourisation of the particles and within an acceptable time frame of less than 4 hours and preferably less than 2 hours, preferably the mixture should be heated to a temperature of between 70 to 100° C. More preferably, the temperature is in the range of from 80 to 97° C., even more preferably in the range of 90 to 96° C.

To achieve low viscosity cellulose-containing particles, i.e. particles with a viscosity of less than 2500 cps, for example 1000 cps or less, with significant decolourisation of the particles, preferably the mixture should be heated to a temperature of between 90 to 100° C. and maintained at this temperature for at least 2 hours until the desired viscosity has been reached and maximum decolourisation has occurred.

If the mixture provided in step (i) is already hot, from the cooking of the vegetable material to provide a pulp, then it is possible that not much more additional heating of the mixture is required. If this is the case, then the heating of step (ii) has already been partially or wholly carried out in step (i). The heating step is terminated by cooling the mixture of step (ii). Preferably the mixture is cooled rapidly.

Step (ii) can also comprise a step whereby the mixture is homogenised. This can occur during heating and results in shortening the length of step (ii). Alternatively or additionally homogenisation can take place after heating. If hot peroxide is a problem for any of the equipment being used then the homogenisation can be carried out after the heating stage is completed and the material has been cooled. In one embodiment, the process of the invention involves homogenisation of the mixture of step (ii) either while the mixture is being maintained at temperature or after the mixture has been cooled down or both.

In one embodiment of the process described herein, the 35% aqueous peroxide solution may be added in an amount of 0.5% by weight or less of the weight of the herbaceous plant material (dry content) and the peroxide treatment step carried out until substantially all of the peroxide has been consumed and then terminated. In this embodiment, a particulate cellulose material with a viscosity of at least 2500 cps (at a 1 wt % solids concentration) is obtained.

In one embodiment of the process described herein, the 35% aqueous peroxide solution may be added in a ratio of 0.5 parts peroxide solution or less to 1 part herbaceous plant material (dry content), for example 0.25 parts peroxide solution to 1 part herbaceous plant material (dry content) and the peroxide treatment carried out until substantially all of the peroxide has been consumed and the reaction immediately terminated. In this embodiment, a particulate cellulose material with a viscosity of at least 2500 cps (at a 1 wt % solids concentration) is obtained.

In one embodiment of the process described herein, the conditions for the peroxide treatment step may be continued after substantially all of the peroxide has been consumed. In one embodiment, the reaction may be continued for at least a further 30 minutes, for example at least 40 minutes, or at least 60 minutes. In this embodiment, a particulate cellulose material with a viscosity of less than about 2500 cps, for example less than about 1000 cps (at a 1 wt % solids concentration) is obtained.

Step (iii)

In step (iii) of the process of the invention a residue comprising the cellulose-containing particles is isolated. This can be achieved by washing and filtering the product from step (ii). The washing removes any soluble breakdown products from the reaction and any excess peroxide reagent. Excess peroxide in the product of step (ii) can also be removed by the addition of a catalyst. Washing can be achieved using a number of different processes such as centrifuge filtration (continuous or batch), microfiltration, filter pressing or simple gravity driven filtration. The peroxide level and the pH can be checked. The peroxide content should preferably be less than 30 mg/l (as measured using a peroxide indicator stick) and pH should preferably be between 6 and 9. Optionally the material can then be pressed or concentrated to lower the water content, for example to 20-50 wt % solids. This pressed cake can then be re-sized by chopping/grinding to form a powder. This powder is capable of rapid re-dispersion and re-hydration when added to water based systems.

Step (iv)

The process of the invention may optionally comprise a further step of contacting the cellulose-containing particles with an oxidant. The oxidant may be sodium hypochlorite. The cellulose-containing particles may be washed with water, and optionally filtered, before being contacted with the oxidant. The washed and filtered cellulose-containing particles may be reconstituted in water prior to being contacted with the oxidant. The oxidant step may be carried out at a temperature of about 60° C. or less. The oxidant may be added in a ratio of about 1 part oxidant to 2 parts solids in aqueous solution. The oxidant may be in the form of a 10% aqueous solution of the active oxidant. The temperature of the oxidant step may be maintained for at least 10 minutes, for example at least 20 minutes, up to about 30 minutes. The resultant cellulose-containing particles may be separated from the oxidant solution and washed with water until free from residual oxidant. Washing can be achieved using a number of different processes such as centrifuge filtration (continuous or batch), microfiltration, filter pressing or simple gravity driven filtration.

Step (v)

The process of the invention may optionally comprise a further step of homogenizing the mixture obtained from step (iii) or step (iv). The step of homogenization may take place on the filtered and dried material from step (iii) or step (iv). The step of homogenization may take place on material obtained from step (iii) or step (iv) which has been reconstituted in water. The homogenization may be carried out until a desired particle size is obtained.

Step (vi)

The process may comprise a further step of concentrating the cellulose particulate material or cellulose containing particles obtained to a particular concentration. The material may be concentrated to a level of, for example at least 5 wt % solids, for example at least about 10 wt % solids, at least about 15 wt %, at least about 20 wt %, at least about 25 wt %, for example about 30 wt % solids. At levels of 15 wt % solids and greater, the material is able to be grated, which may be advantageous in some applications. Lower loading levels result in a paste-like consistency, which may be advantageous in other applications.

Uses of the Cellulose Particulate Materials

Cellulose and cellulose derived materials are known as additives in different industries due at least in part to the viscosity modifying properties. The present invention therefore also relates to water-based, i.e. aqueous systems or compositions comprising the cellulose-containing particles of the present invention. Water-based systems as referred to herein include aqueous solutions and emulsions. Examples are water-based epoxy, acrylic, polyurethane paints and water-based cosmetic systems such as hair shampoos, hair conditioners, and face creams. Further examples are food compositions. Typically in the water-based systems, the cellulose-containing particles of the invention are present in an amount of less than about 10 wt %, less than 5 wt %, for example less than 3 wt %, preferably less than 1 wt %, more preferably 0.05 to 0.2 or 0.5 wt %. The cellulose containing particles of the invention may be present in any of these compositions in an amount of at least 0.05 wt %, at least about 0.2 wt %, at least about 0.5 wt %, at least about 1 wt %, at least about 3 wt %, at least about 5 wt %, at least about 10 wt %. In some embodiments, the cellulose particulate material is incorporated into aqueous compositions in an amount of less than about 2 wt %, for example less than about 1.5 wt %, less than about 1.2 wt %, less than about 1 wt %, less than about 0.5 wt %, less than about 0.4 wt %, less than about 0.3 wt %, less than about 0.25 wt %, less than about 0.2 wt %, less than about 0.1 wt %, less than about 0.05 wt %, less than about 0.04 wt %, less than about 0.03 wt %, less than about 0.02 wt %, for example about 0.01 wt %.

Composite Materials

The invention therefore relates to compositions and composite materials such as concrete and other cementitious materials. The particulate material described herein is particularly useful as a strengthening agent in concrete, other cementitious materials and resin composites.

In one aspect, the invention provides a composite material comprising a resin and up to about 90 wt % plant-derived cellulose particulate material, wherein the plant-derived cellulose particulate material comprises less than 30 wt % extractable glucose; and extractable xylose in an amount of at least 3% of the amount of extractable xylose in the starting plant material. The plant-derived cellulose particulate material may be present in an amount of up to about 85 wt %, for example up to about 80 wt %, up to about 75 wt %, up to about 70 wt %, up to about 65 wt %.

The resin may be a thermoset resin or a thermoplastic resin. The thermosetting resin may be polyester based or epoxide based, but it will be understood that these are examples only and other thermosetting resins such as polyurethanes could also be used. There are many thermoplastic resins used in composite manufacture: polyolefins, polyamides, vinylic polymers, polyacetals, polysulphones, polycarbonates, polyphenylenes and polyimides. In one embodiment, the resin may be an acrylic resin. The resin may be a single resin or the resin may be a blend of more than one resin, including any of the resins described above. The composite material may further comprise one or more binders, for example a hydrophilic binder and/or a hydrophobic binder. Such additives for resin composite materials are known in the art and need no further discussion here.

In one aspect, the invention provides cementitious compositions comprising the cellulose-containing particles or cellulose particulate material. The particulate material may be present in an amount of less than 10 wt %, less than 5 wt %, for example less than about 2 wt %, for example less than about 1 wt %. The cementitious composition may comprise any known cement. For example, the cementitious composition may comprise a hydraulic cement such as Portland cement, which may further be replaced at least in part by, for example, fly ash, slag cement or silica fume to from a Portland cement blend. The cementitious composition may comprise other additives and fillers known in the art such as air entrainment agents, setting retarders, setting accelerators and the like.

In one aspect, the invention provides concrete compositions comprising the cellulose-containing particles or cellulose particulate material. The particulate material may be present in an amount of less than 10 wt %, less than 5 wt %, for example less than about 2 wt %, for example less than about 1 wt %. The concrete composition generally comprises the cellulose particulate material described herein, a cement, and an inert aggregate material such as sand, or a mixture of sand and larger particles such as gravel. The cement may be any type of cement as described previously. Any type of filler/aggregate that is commonly used in the building industry may be used effectively in the context of this invention. Examples of suitable filler/aggregates such as silica sands, calcium carbonate, dolomite, as well as lightweight aggregates such as perlites, polystyrene beads, hollow/expanded glass or ceramic spheres cork, rubber, and the like, and mixture thereof. The proportion of filler/aggregate in the cement or mortar is preferably between 50% and around 85%, more preferably between 60% and around 80%, and most preferably between 65% and around 75% by weight, based on the total dry ingredients. It will be understood that water will subsequently be added in order to produce the final concrete mixture to be cured.

Coatings

Cellulose particulate material is also known to be used in coating compositions as a viscosity modifier or for structural reinforcement to prevent, for example, cracking.

Therefore, in one aspect, the invention provides a coating composition comprising the cellulose-containing particles or cellulose particulate material. The particulate material may be present in an amount of less than 10 wt %, less than 5 wt %, for example less than about 2 wt %, for example less than about 1 wt %. The coating composition may be a paint composition. The coating composition generally comprises a diluent or solvent, typically water, a pigment (for example calcium carbonate, mica, silicas, talcs), a filler (which function may be provided by the pigment or a separate inert material, and one or more further additives such as adhesion promoters, texturizers, UV stabilisers, flatteners or biocides as non-limiting examples. Such coating additives are typically present in the composition in an amount from about 0 to about 18% by weight or up to 18 by weight and from about 1 to about 15% by weight based on the total weight of the formulation.

Food Compositions

Cellulose particulate material is also routinely added to food compositions as a stabiliser, emulsifier or thickener, to modify the viscosity of the food composition and stabilise the food composition. Therefore, in one aspect, the invention provides food compositions comprising the cellulose-containing particles or cellulose particulate material. The particulate material may be present in an amount of less than 10 wt %, less than 5 wt %, for example less than about 2 wt %, for example less than about 1 wt %, less than about 0.5 wt %. The food composition may be an animal feed composition. The food composition may be a baby food composition.

These food compositions may include emulsions, beverages, sauces, soups, syrups, dressings, films, dairy and non-dairy milks and products, frozen desserts, cultured foods, bakery fillings, and bakery cream. The edible food products can additionally comprise diverse edible material and additives, including proteins, fruit or vegetable juices, fruit or vegetable pulps, fruit-flavored substances, or any combination thereof. These food products can also include other edible ingredients such as, for example, mineral salts, protein sources, acidulants, sweeteners, buffering agents, pH modifiers, stabilizing salts, or a combination thereof. Those skilled in the art will recognize that any number of other edible components may also be added, for example, additional flavorings, colorings, preservatives, pH buffers, nutritional supplements, process aids, and the like. The additional edible ingredients can be soluble or insoluble, and, if insoluble, can be suspended in the food product. Routine adjustment of the composition is fully within the capabilities of one having skill in the art and is within the scope and intent of the present invention. These edible food products can be dry mix products (instant sauces, gravies, soups, instant cocoa drinks, etc.), low pH dairy systems (sour cream/yogurt, yogurt drinks, stabilized frozen yogurt, etc.), baked goods, and as a bulking agent in non-aqueous food systems and in low moisture food systems.

In some embodiments, the food compositions can have enhanced storage ability without the need for adjunct stabilizers (outside of the particulate cellulose material used in the compositions). For example, some sauces that lack an adjunct stabilizer, such as xanthan gum, are shown to maintain relative viscosity for extended periods of time, which in some instances is at least six months. The final compositions may be processed by heat treatment in any number of ways. These methods may include, but are not limited to, pasteurization, ultra pasteurization, high temperature short time pasteurization ("HTST"), and ultra high temperature pasteurization ("UHT"). These compositions may also be retort processed, either by rotary retort or static retort processing. Some compositions, such as juice-added or natural or artificially flavored soft drinks may also be cold processed. Many of these processes may also incorporate homogenization or other high shear/high compression methods. There may also be co-dried compositions, which can be prepared in dry-mix form, and then conveniently reconstituted for consumption as needed. The resulting compositions may be refrigerated and stored for a commercially acceptable period of time. In the alternative, the resulting beverages may be stored at room temperature, provided they are filled under aseptic conditions.

Personal Care and Household Products

In accordance with the present invention, the composition may be either a personal care product or a household care product. The personal care product may be a face cream, a shampoo, a conditioner, a sun screen composition, or a moisturiser, for example. When the composition is a personal care product, it may contain at least one active personal care ingredient including, but not limited to, analgesics, anesthetics, antibiotic agents, antifungal agents, antiseptic agents, antidandruff agents, antibacterial agents, vitamins, hormones, corticosteroids, anti-inflammatory agents, vasodilators, kerolytic agents, dry-eye compositions, wound-healing agents, anti-infection agents, as well as solvents, diluents, adjuvants and other ingredients such as water, ethyl alcohol, isopropyl alcohol, propylene glycol, higher alcohols, glycerine, sorbitol, mineral oil, preservatives, surfactants, propellants, fragrances, and essential oils.

Personal care compositions include hair care, skin care, sun care, nail care, and oral care compositions. Examples of additives in personal care compositions include perfume, skin coolants, emollients, deodorants other than perfumes, antiperspirant actives, moisturizing agents, cleansing agents, sunscreen active ingredients. Examples of additives in hair compositions include agents which condition and/or cleanse the hair, cleanse the hair, detangles hair, acts as styling agent, volumizing and gloss agents, color retention agent, anti-dandruff agent, hair growth promoters, hair dyes and pigments, hair perfumes, hair relaxer, hair bleaching agent, hair moisturizer, hair oil treatment agent, and antifrizzing agent.

The composition may be a household care composition, this household care composition including the cellulose particulate material and at least one active household care ingredient. The household care active ingredient must provide some benefit to the user. The household care composition may comprise a laundry detergent, a fabric softener, a dishwasher detergent, a surface cleaning product. The composition may further retreatment compositions, bleaching agents and water softeners, including above all anionic, nonionic, cationic, amphoteric and zwitterionic surfactants, inorganic and organic, water-soluble or water-insoluble builders and co-builders, bleaching agents, more especially peroxy bleaching agents, and active chlorine compounds which are advantageously coated, bleach activators and bleach catalysts, enzymes and enzyme stabilizers, foam inhibitors, redeposition inhibitors, substances which prevent the resoiling of fabrics, so-called soil repellents, and typical inorganic salts, such as sulfates and organic sulfates, such as phosphonates, optical brighteners and dyes and perfumes. In addition, the use of conventional silver protectors is recommended for machine dishwashing detergents. These additives may be incorporated in amounts known to the skilled person.

The cellulose particulate material may be present in an emulsion. The emulsion may comprise an aqueous phase, an oil phase and less than 10 wt % plant-derived cellulose particulate material, wherein the plant-derived cellulose particulate material comprises less than 30 wt % extractable glucose; and extractable xylose in an amount of at least 3% of the amount of extractable xylose in the starting plant material. The emulsion may form the basis of a personal care product, a homecare product or a food composition as previously described.

Paper

Cellulose materials also form the basis of papers and cardboards. Additives are often added in to papers and/or cardboard to enhance physical or chemical properties. In particular, it is desirable to reduce the porosity of a paper or cardboard in order to block permeation of gases, for example odors, fragrances or oxidants, or to block permeation of microbes and viral particles, when packaging food products or cosmetic or perfumed products. Therefore, in one aspect, the invention provides a paper composition comprising less than about 40 wt % plant-derived cellulose particulate material, wherein the plant-derived cellulose particulate material comprises less than 30 wt % extractable glucose; and extractable xylose in an amount of at least 3% of the amount of extractable xylose in the starting plant material. The paper composition may comprise less than about 25 wt %, for example less than about 20 wt %, less than about 5 wt % of the plant-derived cellulose particulate material. Alternatively, the paper composition may comprise more than about 5 wt %, for example more than about 10 wt %, more than about 15 wt %, more than about 20 wt %, more than about 25 wt %, more than about 30 wt %, up to about 40 wt % of the plant-derived cellulose particulate material. The paper composition may comprise a cellulosic pulp known to be useful in paper production, in combination with the cellulose particulate material described herein. The paper composition may further comprise one or more additives such as inorganic fillers, optical brightening agents and pigments.

The invention is further described, but not limited to, the following examples.

EXAMPLES

Example 1

Method for Measuring Viscosity and pH with Reaction Time for Hydrogen Peroxide Treated Root Vegetable Pulp Fresh carrots were peeled, chopped and cooked at 90° C. for 2 hours. The carrots were then homogenised in the cooking liquid, using a Silverson FX homogeniser, to form a pulp with particles less than 500 microns in diameter. The concentration of the pulp was measured, using a moisture analyser, to be 5% solids in water. The batch was then divided into a number of 1 liter samples each contained in a polypropylene bottle with tight fitting lid. These bottles were then placed in to a water bath of hot water regulated to 90° C. The internal temperatures of the bottles were checked periodically. When the temperature reached 90° C., 35% hydrogen peroxide was added to each bottle in a ratio of 1 part 35% peroxide to 1 part carrot solids. The bottles were then left in the water at 90° C. for varying lengths of time. Bottles were taken out of the water bath at intervals and cooled rapidly by placing into a bath of cold water. The pH of the contents was immediately measured using a pH meter. The contents were then poured into a coarse filter made of horticultural frost fleece (pore size approximately 250 microns) and the liquid allowed to drain out. The remaining solids were washed 3 times with clean water. Then the remaining solids were scraped out of the filter and placed into a clean beaker. This pulp was homogenised using a bench top Silverson L5M with a fine slotted collar attached in the head. Homogenisation was carried out for 15 minutes at 8000 rpm. The solids content of the homogenised pulp was then measured using a moisture analyser and adjusted to 1% with fresh water. The temperature at this point was measured as 20° C. The viscosity of the pulp was then measured at a concentration of 1 dry wt % in water using a Brookfield Viscometer DVII+Pro EXTRA, with RV spindle heads, run at 10 rpm. Viscosity was recorded in centipoise (cps). The data from these experiments was then used to plot Viscosity as a function of time and pH as a function of time and this plot in shown in FIG. 1.

Example 2

Preparation of Low Viscosity Cellulose Particulate Material from Sugar Beet 900 g of sugar beet pellets were washed and hydrated by adding them to warm water, with dirty water being drained through a sieve. This sugar beet hydrate is placed in a large bucket in excess water and agitated before being scooped out with a colander and washed with water, to ensure that no stones/grit enter the next stage of processing The washed sugar beet is then cooked for 3 hours at 100° C., before being homogenised using a Silverson FX homogeniser fitted with initially coarse stator screens and moving down to the small holed emulsifier screen (15 min process time for each screen). The solids are measured using an Oxford solids meter and the mixture adjusted to 2% solids by addition of clean water.

The mix is then placed in a 25 liter glass reaction vessel and the dry solids content in the vessel is calculated. Peroxide based on ratio of aqueous peroxide solution (at 35%) to the dry solids of 0.25:1 is added when the mix is heating. The temperature is maintained for 6 hours at 90° C. (once it reaches 90° C.), by which time the pH has dropped from around 5 to 3 or less.

Bleaching is then carried out by re-suspending the washed material in clean water and placing it back in the vessel. Bleaching is performed at 60° C., with a 2:1 bleach (2 parts of bleach solution with 10% active chlorine to 1 part solids, for 30 minutes).

The material is then homogenised for 30 minutes on the fine slotted stator screen of the Silverson FX homogeniser The material is then drained through a filter and pressed between absorbent cloths to a desired final solids content. Resuspension of the solids in water at 1 wt % solids resulted in a viscosity (measured as previously described) of 1500 cps.

Example 3

Comparative Study: Carrots
(A) Process Resulting in High Viscosity Material

Fresh carrots were cooked and homogenised to produce a pulp in water with 5% of carrot pulp solids. Hydrogen peroxide was then added in the ratio of 1 part carrot solids to 0.35 parts of peroxide solids. This mixture formed the reaction liquid. The liquid was then heated to 90° C. and reaction allowed to progress for 1 hr at which point the pH had dropped from 5.2 to 4.75. The resulting liquid was rapidly cooled and washed and filtered at which point the viscosity of a 1% solids mix in water was 3800 cps @ 10 rpm (measured on the Brookfield Viscometer with RV spindle heads, at 20° C.).
(B) Process Resulting in Low Viscosity Material Fresh carrots were cooked and homogenised to produce a pulp in water with 5% of carrot pulp solids. Hydrogen peroxide was then added in the ratio of 1 part carrot solids to 0.35 parts of peroxide solids. This mixture formed the reaction liquid. The liquid was then heated to 90° C. and reaction allowed to progress for 6 hrs at which point the pH had dropped from 5 to 2. The resulting liquid was rapidly cooled and washed and filtered at which point the viscosity of a 1% solids mix in water was 600 cps @ 10 rpm (measured on the Brookfield Viscometer with RV spindle heads, at 20° C.).

Example 4

Product Analysis

Dry material from three stages of the process (start; after peroxide treatment; after sodium hypochlorite treatment) was analysed for extractable monosaccharide/polysaccharide content. The starting plant materials tested were sugar beet and carrot. Comparative examples in the form of (i) cellulosic particulate materials obtained from a sodium hydroxide treatment of carrot as described in WO 2014/017911 ("Cellucomp 8"); and (ii) the material from (i) also subjected to a subsequent bleach treatment ("Cellucomp 9") and subjected to the same analysis.

The test procedure was carried out according to the standard two-step protocol below, which is based on separation of monosaccharides and oligosaccharides from polysaccharides by boiling the sample in an 80% alcohol solution. Monosaccharides and oligosaccharides are soluble in alcoholic solutions, whereas polysaccharides and fibre are insoluble. The soluble components can be separated from the insoluble components by filtration or centrifugation. The two fractions (soluble and insoluble) can then be dried and weighed to determine their concentrations.

The dried materials can then be used for analysis by HPLC, following acid hydrolysis.

(i) Separation of Alcohol Soluble and Insoluble Components

Materials

Dry samples

80% Ethanol

Compressed Nitrogen

Method

For each material sample, 50 mg was extracted three times with 5 ml of 80% ethanol, by boiling the samples in capped glass tubes in 95° C. water bath for 10 min each. After each extraction, the tubes were centrifuged at 5000×g for 5 min, and the supernatants of the three extractions combined for sugar analysis.

The residue and supernatant are oven dried prior to acid hydrolysis. Acid hydrolysis using trifluoroacetic acid degrades pectins, hemicelluloses and highly amorphous regions of cellulose, while acid hydrolysis using 72% (w/v) sulphuric acid degrades all polysaccharides with the exception of highly crystalline regions of cellulose.

(ii)(a) Analysis of Matrix Polysaccharides—Trifluoroacetic Acid Hydrolysis

Materials

Dry samples

Screw cap tubes

2M Trifluororoacetic acid=11.4 g in 50 ml (or 3 ml 99.5% TFA and 17 ml dH$_2$O)

Compressed Nitrogen

Monosaccharide standards

Standard sugar mixture of three monosaccharides (glucose, fructose, xylose). Each sugar is in a 10 mM stock solution (100×). The preparation of the standards is done by pipetting 250, 500, and 750 µl in screw cap vials and evaporating to dryness. Proceed to hydrolysis in the same way as with the samples.

Method

Day 1

Weigh 5 mg of the alcohol insoluble fraction from step (i) in screw cap tubes

Dry all the samples and monosaccharide standards (250 µl, 500 µl, 750 µl)

Day 2

In the fume hood, hydrolyse by adding 0.5 ml 2 M TFA. Flush the vials with dry nitrogen, place the cap, and mix well. Wipe nitrogen nozzle with ethanol tissue between samples to prevent contamination.

Heat the vials at 100° C. for 4 h and mix several times during hydrolysis.

Evaporate completely in centrifugal evaporator or under a nitrogen flush with fume extraction overnight.

Day 3

Add 500 µl of propan-2-ol, mix, and evaporate.

Repeat

Resuspend the samples and standards in 200 µl of dH$_2$O. Mix well.

Centrifuge and transfer the supernatant into a new tube.

Filter supernatant through 0.45 µm PTFE filters prior to HPLC analysis.

(ii)(b) Analysis of Matrix Polysaccharides—Sulphuric Acid Hydrolysis

Materials

Sulphuric acid 72% (w/v) (AR)

Barium hydroxide (150 mM)

Bromophenol blue (1% solution in water)

0.45 µm filters

SPE reverse phase (styrene divinylbenzene); e.g. Strata-X 30 mg, 1 ml volume.

Method

Weight accurately 4 mg of the alcohol insoluble fraction from step (i) into a 2.0 ml screw-top microcentrifuge tube. Alternatively use the dried residue from the matrix sugar digestion.

Add 70 µl of 72% (w/v) sulphuric acid to the screw-top vial. Mix, until solids are dispersed/dissolved.

Incubate in a water bath at 30° C. for 2 hours. Mix samples every 15 minutes.

Add water to reduce the sulphuric acid concentration to 4.6% (w/w)—add 1530 µl water.

Mix well and heat in a block heater at 121° C. for 4 hours. Vortex every 30 minutes.

Cool to room temperature. (Samples may be stored in fridge for up to 2 weeks at this point).

Take 300 µl into a new tube, add 1 µl of 1% bromophenol blue. Partially neutralise by the addition of 0.8 ml 150 mM barium hydroxide. Finish by adding barium carbonate powder. The indicator goes blue.

Centrifuge to eliminate the precipitated barium sulphate (10 min at 10000×g). Transfer supernatant to a new tube. Freeze thaw to finish precipitation and repeat centrifugation (total volume 1050 µl).

Prior to HPLC, the samples (700 µl aliquot) are passed on a reverse phase column (e.g. strata X 30 mg) and filtered through a 0.45 µm filter.

The results of these analyses, with respect to xylose content and glucose content are shown in Table 1 below. Quantitative data can be obtained by injection of a known amount of a reference monosaccharide, for example glucose or xylose, as is routine in the art.

TABLE 1

| Sample | Material | Process | Sample taken for TFA hydrolysis (mg) | Peak area | xylose (mg) | % xylose release |
|---|---|---|---|---|---|---|
| Cellucomp 1 | Sugar Beet | Start Material | 4.8 | 30274 | 0.955 | 19.90 |
| Cellucomp 2 | Sugar Beet | Peroxide Process | 5.7 | 2880 | 0.089 | 1.56 |
| Cellucomp 3 | Sugar Beet | Full Process | 5.1 | 3281 | 0.102 | 2.00 |
| Cellucomp 4 | Sugar Beet | Full Process with extra wash | 5.4 | 3161 | 0.098 | 1.82 |
| Cellucomp 5 | Carrot | Start Material | 5.4 | 3230 | 0.100 | 1.86 |
| Cellucomp 6 | Carrot | Peroxide Process | 4.9 | 1334 | 0.040 | 0.82 |
| Cellucomp 7 | Carrot | Full Process | 4.7 | 1530 | 0.046 | 0.99 |
| Cellucomp 8 | Comparative Example (Carrot) | NaOH + heat | 5.6 | 1021 | 0.030 | 0.54 |
| Cellucomp 9 | Comparative Example (Carrot) | Cellucomp 8 followed by bleach | 4.6 | 1302 | 0.039 | 0.85 |
| Cellucomp 10 | Sugar Beet (low viscosity) | Full process | 4.9 | 1119.3 | 0.033 | 0.68 |

| Sample | Material | Process | Sample taken for H2SO4 hydrolysis (mg) | Peak area | glucose (mg) | % glucose release |
|---|---|---|---|---|---|---|
| Cellucomp 1 | Sugar Beet | Start Material | 4.8 | 351 | 0.353 | 7.31 |
| Cellucomp 2 | Sugar Beet | Peroxide Process | 5.7 | 1121 | 0.739 | 12.99 |
| Cellucomp 3 | Sugar Beet | Full Process | 5.1 | 1830 | 1.098 | 21.57 |
| Cellucomp 4 | Sugar Beet | Full Process with extra wash | 5.4 | 1654 | 1.012 | 18.71 |
| Cellucomp 5 | Carrot | Start Material | 5.4 | 858 | 0.605 | 11.26 |
| Cellucomp 6 | Carrot | Peroxide Process | 4.9 | 1525 | 0.948 | 19.29 |
| Cellucomp 7 | Carrot | Full Process | 4.7 | 1724 | 1.044 | 22.26 |
| Cellucomp 8 | Comparative Example (Carrot) | NaOH + heat | 5.6 | 3578 | 1.987 | 35.43 |
| Cellucomp 9 | Comparative Example (Carrot) | Cellucomp 8 followed by bleach | 4.6 | 2595 | 1.489 | 32.33 |
| Cellucomp 10 | Sugar Beet (low viscosity) | Full process | 4.9 | 2247 | 1.311 | 26.76 |

Example 5

Preparation of a Low Viscosity Cellulose Particulate Material and Measurement of the Bending Strength and Stiffness of a Composite of the Low Viscosity Cellulose Particulate Material and a Water Based Epoxy Resin.
Method The paste from the filter of Example 2 was mixed with a water based epoxy resin called Beckapox 386W/52WA with Beckapox 2188W/55WA hardener. The ratio of carrot solids to epoxy solids was 1:0.3. Further water was then added while stirring in a dough mixer until the material reached a pourable consistency.

The paste of carrot material and epoxy was then poured into a polypropylene tray to a depth of around 5 mm. The tray was placed in a fan heated drying chamber and dried at 30° C. for 2 days, at which point the material had dried into a thin strong sheet. The sheet was peeled from the tray and further dried and cured in an oven at a temperature of 120° C.

The dried and cured sheet was cut into rectangular pieces 2 cm wide and 8 cm long. These strips were then weighed and painted on both sides with solvent based epoxy EOP504+ hardener and sandwiched on top of one another in a metal mound. A lid was placed on the mould and the strips of sheet and epoxy were pressed together by pacing the whole mould in a hydraulic press and pressing down the lid. A maximum pressure of 0.25 tons was applied. The arrangement was left under pressure overnight to cure and further cured in an oven at 60° C. for 8 hours.

The beam shaped sample of carrot material and epoxy was then weighed and the carrot extract content calculated to be 65%.

The beam was then polished on a sander to ensure a regular beam shape. The dimensions were then measured and the beam was then tested in 3 point bending using an Instron test machine. The beam was bent until failure and Instron software was then used to calculate the Stiffness, strength and failure strain of the sample.
Results The bending stiffness of the sample was found to be 8.756 GPa, the strength was 140 MPa and the yield strain was 2.164%. These results compare very favourably with randomly oriented chopped strand glass fibre embedded in epoxy resin and therefore demonstrate that the vegetable fibre material made by this method has significant potential as a reinforcing agent in curable resin systems.

Example 6

Cementitious Materials/Concrete

The cellulose particulate material described herein was tested for its suitability in composite materials, particularly cementitious materials such as concrete and mortar.

The cellulose particulate material was incorporated into a mortar mix in amounts of 1 wt %, 5 wt % and 10 wt % as set out below. The cement product used was a decorative mortar called Enduit Béton Coloré available from Mercardier.
Composition:
4.3 kg cement powder
1 kg acrylic resin binder
1 wt % or 5 wt % cellulose particulate material (CPM)

The indentation strength of the composite material was tested using a 2 mm thick sample of material. The test used a 62.5 MPa punch with a 1 cm diameter punch die. The results are shown in Table 4 below:

TABLE 4

| | Results in MPa | | | |
|---|---|---|---|---|
| Composition | Sample 1 | Sample 2 | Sample 3 | Average |
| EBC | 29.5 | 26.5 | 29.5 | 28.5 |
| EBC + 1% CPM | 36.5 | 37.5 | 34.5 | 36.17 |

TABLE 4-continued

| | Results in MPa | | | |
|---|---|---|---|---|
| Composition | Sample 1 | Sample 2 | Sample 3 | Average |
| EBC + 5% CPM | 30.5 | 35 | 31.5 | 32.33 |
| EBC + 10% CPM | 29 | 30 | 26.5 | 28.5 |

This data shows that inclusion of up to 5 wt % of the cellulose particulate material described herein led to an improvement in the strength of the material, demonstrating that the cellulose particulate material is able to strengthen or reinforce inorganic composite materials such as concrete.

Example 7: Paper Compositions

A paper composition comprising differing amounts of the cellulose particulate material (CPM) described herein was tested for opacity and porosity.

Inclusion of the cellulose particulate material described herein decreased porosity relative to a base paper formed from a standard cellulose. Decreasing porosity of a paper composition provides advantages for food, cosmetic and fragrance-type packaging where permeation of gases, microbes and other substances is undesirable.

From the above examples, it can be seen that the cellulose particulate materials described herein, and the processes for producing such cellulose particulate materials find utility in many different applications.

The invention claimed is:

1. A process for preparing cellulose-containing particulate material which has a viscosity at a concentration of 1 dry wt % in water of less than 2500 cps, the process comprising the steps of:
   contacting herbaceous plant material with a peroxide reagent and water;
   (ii) heating the mixture from (i) to a temperature of from 30 to 110° C. and maintaining said mixture at a temperature of from 30 to 110° C. until the pH of the mixture has dropped by at least 2 pH units;
   (iii) isolating the cellulose-containing particles; and
   (iv) reducing the water content of the product of step (iii).

2. A process according to claim 1, wherein the herbaceous plant material comprises greater than 30% by volume of parenchymal cell material.

3. A process according to claim 1, wherein the herbaceous plant material comprises less than 10 wt % lignocellulose.

4. A process according to claim 1, wherein the plant material is a root vegetable.

5. A process according to claim 1, wherein the plant material is a potato.

6. A process according to claim 1, wherein step (i) includes mechanically treating the herbaceous plant material so that it comprises particles with a major dimension of less than 10 mm.

7. A process according to claim 1, wherein step (ii) involves mechanically homogenizing the mixture while the mixture is being maintained at said temperature and/or wherein step (ii) involves cooling down the mixture after the period of time is over and then mechanically homogenizing the mixture.

8. A process according to claim 1, wherein, in step (ii) the mixture is heated to a temperature of from 70 and 100° C. and maintained at a temperature of from 70 and 100° C.

9. A process according to claim 1, wherein the process is carried out in the absence of an alkali or acid reagent.

10. A process according to claim 1, wherein the process comprises a further step (v) of contacting the cellulose-containing particles with an oxidant.

11. A process according to claim 1, wherein the process is carried out in the absence of a pH-modifying additive.

12. A process according to claim 1, wherein the only chemical treatment used to break down the herbaceous plant material is the peroxide chemical treatment of step (i).

13. A composition comprising less than about 10 wt % plant-derived cellulose particulate material, wherein the plant-derived cellulose particulate material comprises less than 30 wt % extractable glucose; and extractable xylose in an amount of at least 3% of the amount of extractable xylose in the starting plant material.

14. The composition of claim 13, wherein the composition is a cement composition, further comprising a binder.

15. The composition of claim 13, wherein the composition is a concrete composition, further comprising an aggregate material.

16. The composition of claim 13, wherein the composition is a paint composition, further comprising a binder.

17. The composition of claim 13, wherein the composition is a food composition.

18. The composition of claim 13, wherein the composition is a cosmetic composition, further comprising a binder.

19. Paper comprising less than about 40 wt % plant-derived cellulose particulate material, wherein the plant-derived cellulose particulate material comprises less than 30 wt % extractable glucose; and extractable xylose in an amount of at least 3% of the amount of extractable xylose in the starting plant material.

* * * * *